United States Patent [19]

Baleiko et al.

[11] Patent Number: 4,761,393

[45] Date of Patent: Aug. 2, 1988

[54] METHOD FOR PLACING A CATALYTICALLY ACTIVE ALKALI METAL ON A CATALYST SUPPORT

[75] Inventors: Marc O. Baleiko, Naperville; Edward F. Rader, Wheaton, both of Ill.

[73] Assignee: Amoco Corporation, Chicago, Ill.

[21] Appl. No.: 78,374

[22] Filed: Jul. 27, 1987

[51] Int. Cl.$^4$ .................. B01J 31/04; B01J 21/08; B01J 23/04

[52] U.S. Cl. .................. 502/170; 502/174; 502/201; 502/208; 502/214; 502/224; 502/227; 502/242; 502/243; 502/512

[58] Field of Search .............. 502/170, 174, 201, 208, 502/224, 227, 214, 242, 243, 512

[56] References Cited

U.S. PATENT DOCUMENTS 3,520,915  7/1970  Kominami et al. ............ 502/242 X
3,840,587  10/1974  Pearson ...................... 502/243 X
3,840,588  10/1974  Pearson ...................... 502/243 X
4,631,264  12/1986  Hagen ......................... 502/243

Primary Examiner—Patrick P. Garvin
Attorney, Agent, or Firm—Reed F. Riley; William H. Magidson; Ralph C. Medhurst

[57] ABSTRACT

A method for placing catalytically active alkali metal ion on a catalyst support to make an in situ catalyst is disclosed. Specifically, the method contemplates providing a quantity of a suitable catalyst support in a particulate form, providing a gaseous feed stream containing a predetermined amount of the alkali metal ion in the form of a volatile alkali metal compound, and contacting the catalyst support with the volatile alkali metal ion-containing feed stream for a time period sufficient to deposit at least some of the alkali metal present in the feed stream onto the thus-contacted catalyst support.

8 Claims, No Drawings

METHOD FOR PLACING A CATALYTICALLY ACTIVE ALKALI METAL ON A CATALYST SUPPORT

TECHNICAL FIELD OF THE INVENTION

The present invention relates to the synthesis of an unsaturated carboxylic acid by the condensation of a saturated carboxylic acid with formaldehyde in the presence of a catalyst. More particularly, the present invention is directed to a method for producing the catalyst in situ and under condensation reaction conditions.

BACKGROUND OF THE INVENTION

A saturated carboxylic acid such as propionic acid (PA) can be catalytically reacted with formaldehyde (FA) in the vapor phase to produce an alpha, beta-ethylenically unsaturated carboxylic acid such as methacrylic acid (MA), and water. Catalysts to effect such reactions are well known in the art. See, for example, U.S. Pat. Nos. 3,014,958 to Koch et al.; 3,247,248 to Sims et al; 3,840,587 to Pearson; 3,933,888 to Schlaefer; 4,147,718 to Gaenzler; and 4,631,264 to Hagen. Such catalysts typically comprise a catalyst support and a catalytically active ingredient on the support. The produced unsaturated carboxylic acid can be esterified to a commercially useful unsaturated carboxylic acid ester such as methyl methacrylate (MMA).

MMA is a widely-used monomer. Illustrative of the many products that can be made from MMA-derived polymers are advertising displays, lighting fixtures, glazing materials, structural panels, and the like, molding resins for automobile tail-light lenses, plumbing fixtures, and the like, as well as constituents of a variety of surface coatings, adhesives, inks, floor polishes, and the like.

In carrying out most catalyzed chemical processes, catalysts are made in their final forms before being introduced into the process. However, it can be beneficial to produce the final catalyst form in situ. That is, produce it in the reactor as one or all of the process feeds are fed to the reactor, often under reaction conditions. Of course this technique is only useful if the catalyst made in this way is about equal to or superior to the catalyst made before introduction into the process. This requirement is a severe one as emphasized by the lack of catalysts produced in this way. Such an in situ produced catalyst, if a way is found to make it, can vastly improve economics, and, if the catalyst can be continually regenerated in the same way during the process, lifetime can be greatly extended with an additional resulting improvement in process economics.

The present invention provides a method for producing in situ an alkali metal ion-based catalyst for the condensation of formaldehyde and an alkanoic acid to form an alpha, beta-ethylenically unsaturated acid.

SUMMARY OF THE INVENTION

The present invention relates to a method for placing catalytically active alkali metal on a catalyst where the alkali metal is present on a suitable support and in the +1 oxidation state. Preferably, the catalyst support is partly or wholly constituted by a porous, siliceous material in particulate form, optionally mixed with another material such as particulate tin (IV) oxide. A support containing both the porous, siliceous material above and particulate tin (IV) oxide is called herein a "mixed-oxide." Such a catalyst can be utilized to produce an alpha, beta-ethylenically unsaturated carboxylic acid via vapor-phase condensation of a saturated carboxylic acid with formaldehyde.

The method of the present invention contemplates contacting a particulate catalyst support with a gaseous feed stream containing a volatile alkali metal compound at an elevated temperature and for a time period sufficient to deposit at least some of the alkali metal present in the feed stream onto the thus-contacted catalyst support to make an active catalyst. Preferably, the gaseous feed stream is constituted by at least the saturated carboxylic acid.

DETAILED DESCRIPTION OF PREFERRED EMBODIMENTS

While the present invention is susceptible to embodiment in various forms, described hereinbelow are a number of illustrative embodiments of the present invention. The present disclosure is to be considered as an exemplification of the present invention without limitation to the specific embodiments discussed, however.

In the ensuing detailed description, certain terms will be utilized for purposes of conciseness and to otherwise elucidate the features and advantages of the present invention. These terms are defined hereinbelow.

The term "activity" as herein used in connection with activity of a catalyst means the relative ease or difficulty of the catalyst to effect chemical conversion of the reactant or reactants to the desired product or products at a given temperature and pressure.

The term "catalyst" as used herein broadly means a substance which increases the rate at which a thermodynamically-allowable chemical reaction takes place. Typically, relatively small amounts of catalyst markedly affect the rate of a given chemical reaction.

The term "colloidal silica" as used herein describes a dispersion of substantially millimicron-size silica ($SiO_2$) particles in an aqueous or organic vehicle. Colloidal silica is also sometimes referred to as "silica sol." An illustrative silica sol is one commercially available from the Nalco Chemical Company, Oakbrook, Illinois 60521, under the designation Nalco 1034-A silica sol. Nalco 1034-A silica sol has a silica concentration of about 34 weight percent, based on the weight of the silica sol, a mean silica particle size of about 20 nanometers (i.e., about 200 Angstroms), a pH of about 3, a particulate surface area of about 150 $m^2$/gram of $SiO_2$, a viscosity of about 10 centipoises, and a sodium content of less than about 0.05 wt. % $Na_2O$, based on the weight of the silica sol.

The term "drying" as used herein means subjecting the material to be dried to a temperature of no more than about 250° C. (about 480° F.).

The term "calcining" as used herein means subjecting a material to a temperature of at least about 250° C. (about 480° F.).

The term "silica gel" as used herein describes a coherent, rigid, continuous three-dimensional matrix or structure of generally spherical particles of silica having a pore volume of between about 0.5 and 3.5 cc/g and an average pore diameter of between about 80 and about 600 Angstroms.

The term "WHSV" as used herein means weight hourly space velocity, and is expressed as grams of feed per gram of catalyst per hour.

Additional definitions include the following equations.

Yield (Y), based on propionic acid:

$$\% \ Y \ (PA) = \frac{\text{mols of } MA \text{ produced}}{\text{mols of } PA \text{ in feed}} \times 100$$

Yield (Y), based on formaldehyde:

$$\% \ Y \ (FA) = \frac{\text{mols of } MA \text{ produced}}{\text{mols of } FA \text{ in feed}} \times 100$$

Methacrylic acid selectivity (S), based on propionic acid:

$$\% \ S \ (PA) = \frac{\text{mols of } MA \text{ produced}}{\text{mols of } PA \text{ converted}} \times 100$$

Methacrylic acid selectivity (S), based on formaldehyde:

$$\% \ S \ (FA) = \frac{\text{mols of } MA \text{ produced}}{\text{mols of } FA \text{ converted}} \times 100$$

Conversion (C):

$$\% \ C = \frac{\% \ Y}{\% \ S} \times 100$$

As briefly mentioned above, the present invention contemplates a method for placing a given amount of a catalytically active alkali metal on a support to make a catalyst suitable for the vapor-phase condensation of a saturated carboxylic acid with formaldehyde. Such a catalyst is constituted by the alkali metal in the +1 oxidation state which is distributed on a suitable particulate catalyst support. The catalyst support material can be, for example, (1) an alumina or titania extrudate, (2) an alumina, barium carbonate, calcium carbonate, kieselguhr (diatomaceous earth), silica-alumina, porous silica gel, strontium carbonate, tin oxide, or titania powder, (3) an alumina pellet, ring, or sphere, (4) a porous silica gel granule, (5) an ion-exchange resin and (6) porous silica gel mixed with particulate tin (IV) oxide (mixed-oxide) such as described in U.S. application Ser. No. 891,755, filed July 31, 1986 and now abandoned, which application is specifically incorporated herein by reference. Commercially available extrudates, granules, spheres and pellets of the foregoing substances and varying in size from about 1/32 to about ¼ inches in diameter, as well as finely-divided powders, and the like are suitable catalyst supports for purposes of the present invention.

The catalytically-active alkali metals that can be loaded onto the desired support in the process of the instant invention are sodium, potassium, rubidium, and cesium.

The preferred alkali metal is cesium and the preferred catalyst support is constituted by a porous, siliceous material, such as calcined or uncalcined silica gel, in particulate form, or porous silica gel mixed with particulate tin (IV) oxide (mixed-oxide). The preferred form of the catalyst support is granules or extrudate.

Illustrative of the alkali metal-containing compounds that can be utilized using cesium as an example are cesium carbonate ($Cs_2CO_3$), cesium bicarbonate ($CsHCO_3$), cesium formate [$Cs(CHO_2.H_2O)$], cesium fluoride (CsF), cesium nitrate ($CsNO_3$), cesium hydroxide (CsOH), cesium oxide ($Cs_2O$), cesium phosphate ($Cs_3PO_4$), cesium acetate [$CsC_2H_3O_2$], and cesium propionate [$CsC_3H_5O_2$]. Cesium hydroxide, cesium carbonate, and cesium propionate are particularly preferred for this purpose.

Such a catalyst is utilized to produce an alpha, beta-ethylenically unsaturated carboxylic acid, such as methacrylic acid, via vapor-phase condensation of a saturated carboxylic acid, such as propionic acid, with formaldehyde, in the presence of the catalyst and at vapor-phase condensation reaction conditions.

In particular, the method of the present invention contemplates providing a quantity of the desired catalyst support, providing a feed stream constituted by a gaseous carrier, such as the saturated carboxylic acid which is to be condensed with formaldehyde, and a predetermined amount of the alkali metal in the form of the desired volatile alkali metal compound, and contacting the catalyst support with the volatile alkali metal-containing feed stream. The contacting is effected at an elevated temperature, usually at the vapor-phase condensation reaction conditions, and for a time period sufficient to deposit at least some of the alkali metal present in the feed stream onto the catalyst support.

If the feed stream contains an appreciable amount of water, it is desirable but not necessary to dry the feed stream before contacting the catalyst support therewith.

The alkali metal concentration in the feed stream can be in the range of about 10 p.p.m. by weight to about 1000 p.p.m. by weight, and preferably from about 50 ppm by weight to about 300 ppm by weight. The preferred alkali metal concentration in the feed depends upon the rate at which the catalyst support is to be activated and on the desired level of alkali metal ion to be placed on the catalyst support. It is desirable to keep the concentration of the alkali metal in the feed at a minimum needed to build up the catalytic activity in a reasonable length of time when the catalyst support is siliceous so as to avoid a mineralizing effect and an attendant loss of surface area over a prolonged period of time. A relatively high concentration of the alkali metal compound can be introduced into the feed stream initially, and thereafter a maintenance concentration provided for the desired extended time period. Optionally, the amount of the volatile alkali metal compound present in the feed stream can be modulated to maintain an alkali metal concentration on the catalyst in the desired range.

The present invention contemplates the in situ production of an active catalyst under vapor-phase condensation reaction conditions. Specifically contemplated is a method which comprises providing a reactor containing a catalyst support (initially substantially free from a catalytically active constituent), passing a feed stream containing the volatile alkali metal-bearing compound (or a volatile alkali metal-containing precursor thereof) through the reactor while maintaining vapor-phase condensation reaction conditions in the reactor, and depositing at least some of the alkali metal from the feed stream onto the catalyst support, thereby producing the catalyst in situ and under vapor-phase condensation reaction conditions.

The present invention is illustrated further by the following example in which the conditions described herein below were maintained and the following equipment and procedures were used, unless otherwise indicated.

Paraformaldehyde was used as the FA source. However, in the conversion of PA with FA in the presence of the catalyst to produce MA, any suitable source of formaldehyde can be used, such as formalin, methanolic formaldehyde, substantially anhydrous formaldehyde, trioxane and the like.

Reactor effluent samples were analyzed by gas chromatography (GC). An internal standard technique was used. That is, the GC response for each of the organic components in the reactor effluent was based upon the known response of the GC to an internal standard added to the sample. Actual PA titrations indicated that the propionic acid used in the feed was at least about 99.6 to about 99.9% pure.

EXAMPLE

In Situ Production of an Active Catalyst Under Condensation Reaction Conditions A reactor was charged with about 20 grams of acid-washed, uncalcined particular silica gel support derived from Nalco 1034-A silica sol having a particle size of about 20 to 40 mesh (U.S. Sieve Series).

The reactor, a 1" O.D. titanium tube about 6" long, immersed in a fluidized sand bath heater, was brought to an inlet reaction temperature of about 335° C. to about 360° C. A feed stream comprising propionic acid and paraformaldehyde was fed to the reactor at a rate of about 225 grams per hour (WHSV about 11 hr.$^{-1}$) through a coil of ¼" O.D. titanium tubing about 12 ft long immersed in the sand bath and serving to fully vaporize the feed before entering the reactor at the inlet reactor temperature. The feed stream included about 115 p.p.m. by weight cesium added in the form of CsOH. Over a period of about 26 hours, the conversion of propionic acid to methacrylic acid was observed to increase from zero percent to about 23%. The feed was stopped after about 35 hours because the reactor exotherm indicated a reduction of catalyst activity, an occurrence commonly associated with the formation of coke on the catalyst. The reactor was fed a mixture of nitrogen and air at a temperature of about 370° C. for about 60 hours to assure removal of the coke. The same feed was restarted and continued under about the same conditions as above for about another 24 hours when again the reactor exotherm indicated a reduction in catalyst activity. During this period analytical results indicated that the selectivity to methacrylic acid was about 83%, S(PA), about 33%, C(PA). The experimental run was terminated, and the catalyst analyzed. The weight percentage of cesium on the catalyst, comprising the cesium-containing deposited compound together with the silica support, was found to increase from 0 wt. % Cs to about 5.7 wt. % Cs, based on the weight of the catalyst. Accordingly, an active catalyst had been produced in situ under vapor-phase condensation reaction conditions.

What is claimed is:

1. A method for preparing an alkali metal ion-bearing particulate siliceous catalyst suitable for enhancing the vapor-phase condensation of a gaseous, saturated carboxylic acid with formaldehyde, which method comprises:

providing a bed containing a particulate siliceous catalyst support;

providing a gaseous carrier stream containing at least said saturated carboxylic acid;

introducing into said gaseous carrier stream a volatile alkali metal compound to produce a gaseous admixture containing said gaseous carboxylic acid and said volatile alkali metal compound; and intimately contacting said admixture and said bed while maintaining the vapor-phase condensation reaction conditions in said bed for a time period sufficient to deposit at least some of the alkali metal present in said feed stream onto the thus contacted catalyst support.

2. The method in accordance with claim 1 wherein the saturated carboxylic acid is propionic acid, and wherein the volatile alkali metal compound is cesium hydroxide.

3. The method in accordance with claim 1 wherein the saturated carboxylic acid is propionic acid, and wherein the volatile alkali metal compound is cesium propionate.

4. The method in accordance with claim 1 wherein the alkali metal ion is cesium.

5. The method in accordance with claim 1 wherein the cesium concentration in the feed stream is about 10 p.p.m. by weight to about 1000 p.p.m. by weight cesium.

6. The method in accordance with claim 1 wherein the cesium concentration in the feed stream is about 50 p.p.m. by weight to about 300 p.p.m. by weight.

7. The method in accordance with claim 2 wherein said bed containing a particulate siliceous catalyst support contains particulate tin (IV) oxide.

8. The method in accordance with claim 3 wherein said bed containing particulate siliceous catalyst support contains particulate tin (IV) oxide.

* * * * *